(12) United States Patent
Peck (10) Patent No.: US 7,997,408 B2
(45) Date of Patent: Aug. 16, 2011

(54) RAPID OPENING PACKAGING SYSTEM FOR AIRWAY DEVICES

(76) Inventor: Michael Jonathan Peck, Rockville, MD (US)

(*) Notice: Subject to any disclaimer, the term of this patent is extended or adjusted under 35 U.S.C. 154(b) by 230 days.

(21) Appl. No.: 12/338,830

(22) Filed: Dec. 18, 2008

(65) Prior Publication Data
US 2009/0165793 A1    Jul. 2, 2009

Related U.S. Application Data

(60) Provisional application No. 61/017,679, filed on Dec. 30, 2007.

(51) Int. Cl.
*A61B 19/02* (2006.01)

(52) U.S. Cl. ........................ 206/438; 206/570

(58) Field of Classification Search ............... 206/438, 206/484, 570–572, 459.1, 363–370
See application file for complete search history.

(56) References Cited

U.S. PATENT DOCUMENTS

| | | | | | |
|---|---|---|---|---|---|
| 3,604,616 | A | * | 9/1971 | Greif | 206/439 |
| 3,696,920 | A | * | 10/1972 | Lahay | 206/370 |
| 3,814,103 | A | * | 6/1974 | Fettel et al. | 128/207.18 |
| 3,872,515 | A | * | 3/1975 | Miner et al. | 2/168 |
| 4,116,338 | A | * | 9/1978 | Weichselbaum | 206/438 |
| 6,360,888 | B1 | * | 3/2002 | McIvor et al. | 206/305 |
| 6,786,515 | B2 | * | 9/2004 | Franko, Sr. | 283/81 |
| 7,073,666 | B2 | * | 7/2006 | Arndt | 206/524.8 |

* cited by examiner

*Primary Examiner* — J. Gregory Pickett (57) ABSTRACT

The present invention relates to a packaging system for airway devices that permits their rapid access. In particular, the packaging system is capable of maintaining the device in storage under sterile conditions, yet be capable of facilitating rapid unpackaging and use.

20 Claims, 5 Drawing Sheets

RAPID OPENING PACKAGING SYSTEM FOR AIRWAY DEVICES

CROSS-REFERENCE TO RELATED APPLICATIONS

This application claims priority to U.S. Patent Application Ser. No. 61/017,679 (filed on Dec. 30, 2007, and presently pending), which application is herein incorporated by reference in its entirety.

BACKGROUND OF THE INVENTION

1. Field of the Invention

The present invention relates to a packaging system for airway devices that permits their rapid access. In particular, the packaging system is capable of maintaining the device in storage under sterile conditions, yet be capable of facilitating rapid unpackaging and use.

2. Description of Related Art

The airway of a human being includes the throat and windpipe, and leads to the lungs. Control and management of a patient's airway are required under a variety of circumstances.

During the administration of general anesthesia, in particular, or as a result of trauma or injury, loss of consciousness and tracheal muscle tone may require the use of an artificial airway to maintain proper patient ventilation. A wide variety of devices are currently available for this purpose (see, e.g., United States Patent Publications Nos. 2002/0011249, 2002/0189618, 2005/0016529, 2005/0039756, 2005/0199244, 2007/0028923, and 2008/0029100; U.S. Pat. Nos. 5,937,859; 6,070,581; 6,119,695; 6,311,688; 6,427,686; 6,705,321; 6,830,049; 7,096,868; and 7,357,845; PCT Publications WO9816273, WO00/30707, WO05087300 and WO08/123,934). In brief, such airway devices can be categorized as face masks, endrotracheal tubes or as pharyngeal airways.

Face masks cover the mouth and nose and provide a port for connection to a ventilation means. They provide a non-invasive means for short term airway control, particularly in patients free of airway obstructions or tracheal damage. Endotracheal tubes are tubes that are inserted into the trachea through the mouth or nose. The devices can comprise an inflatable cuff or balloon which permits the device to seal against the interior surface of the trachea. This approach avoids the deficiencies of face masks because it includes the provision of a conduit traversing the pharynx, and forms an effective seal against the airway, allowing positive pressure ventilation, and protection against aspiration of stomach contents (see, U.S. Pat. No. 6,070,581). Endotracheal tubes can, however, be difficult to insert and properly position. Moreover, insertion is invasive and can be particularly problematic for patients who are not deeply sedated. Pharyngeal airway devices generally comprise a tube with a cuff to seal against the pharyngeal wall at the base of the tongue (see, e.g., U.S. Pat. Nos. 3,814,103; 3,908,665; 4,054,135; 4,067,331; 4,068,658; 4,069,820; 4,090,518; 4,338,930; 5,443,063; 5,743,258; 5,653,229; PCT Publication No. WO95/06492).

Accurate placement of an airway device can be a very difficult task for the clinician and can be a traumatic event for the patient. When a patient is under anesthesia, or has lost consciousness for other reasons, the tongue and tissues of the throat relax and fall back, effectively obstructing the flow air from the mouth or nose to the laryngeal opening. This same relaxation of the tongue makes it difficult to pass an airway device along the back of the tongue, into the throat.

The difficulties attending to the use of airway devices is compounded by the often urgent and exigent circumstances in which they must be employed, especially in the case of trauma patients. Choosing an airway device appropriate for use in a given medical procedure may be difficult, if not impossible, to accomplish in advance of examination. As the devices as typically stored in sterile packaging, the time and complexity of removing the device from the packaging materials can compound the complexity of the procedure and delay installation of the device. Thus, it is desirable to employ a packaging system capable of storing the device so that it will be rapidly ready for use.

A wide variety of packaging systems has been developed for medical devices. Such systems include transparent blister trays (see, e.g., U.S. Pat. No. 7,055,694; United States Patent Application Publications Nos. 2007/0209957 and 2004/0195145); capped containers (United States Patent Publication No.: 2006/0200046); sterilizable pouches (see, e.g., United States Patent Application Publication No: 2007/0084144; PCT Publication No.: WO05087302); tab-closing envelopes (see, e.g., United States Patent Application Publication No: 2004/0020795); and edge-sealed, sandwiched sheet coverings (see, e.g., U.S. Pat. Nos. 4,941,308; 4,863,016). Such edge-sealed, sandwiched sheet coverings have become a conventional means for packaging medical devices.

Despite all such advances, a need thus remains for a packaging system that will permit a physician or emergency responder to rapidly access a desired packaged airway device so that it can be quickly and efficiently provided to the patient. The present application is directed to this and other uses.

SUMMARY OF THE INVENTION

The present invention relates to a packaging system for airway devices that permits their rapid access. In particular, the packaging system is capable of maintaining the device in storage under sterile conditions, yet be capable of facilitating rapid unpackaging and use.

In detail, the invention provides a packaging system for sterilely storing an airway device, wherein the system comprises a covering capable of being sealed to itself, or to a second covering, to thereby form a closed container for sterilely storing the airway device; wherein the container possesses an external surface that has been specially adapted to permit a user to tear open the container and retrieve the stored airway device.

The invention particularly includes the embodiments of such packaging system wherein the closed container is formed from a single covering sealed upon itself or wherein the closed container is formed from sealing a first covering to a second covering.

The invention further includes the embodiments of such packaging systems wherein at least a portion of an external surface of a covering of the container is transparent to permit inspection of a stored airway device.

The invention further includes the embodiments of such packaging systems wherein a portion of an external surface of a covering of the container comprises an Information Panel that provides a user with information regarding an airway device to be stored in the container.

The invention further includes the embodiments of such packaging systems wherein the information is partially provided as a color, a shape, or a texture.

The invention further includes the embodiments of such packaging systems wherein a covering of the container contains an embedded material, which, when pulled, causes the external surface to tear, and thereby permit retrieval of a stored airway device and/or wherein a covering of the container is pseudo-perforated such that when the pseudo-perforations are stressed, the external surface tears, and thereby permit retrieval of a stored airway device.

The invention further includes the embodiments of such packaging systems wherein a portion of an external surface of a covering of the container comprises a Sensor Panel that provides a user with information regarding a functionality of an airway device to be stored in the container. The invention further includes the embodiments of such packaging systems wherein the Sensor Panel comprises a sensor of carbon dioxide or a temperature sensor.

The invention further includes the embodiments of such packaging systems wherein a portion of an external surface of a covering of the container comprises an Auxiliary Panel that provides a user with means to heat or to illuminate a stored airway device.

The invention further includes the embodiments of such packaging systems wherein the system additionally comprises a hypoallergenic strap, tape, sterile non-allergenic gloves, or an LED flashlight.

The invention is additionally directed to an airway device kit, comprising an airway device sterilely enclosed in a closed container, wherein the container is formed from a covering sealed to itself or to a second covering, wherein a covering of the container possesses an external surface that has been specially adapted to permit a user to tear open the container and retrieve the stored airway device.

The invention further includes the embodiment of such an airway device kit wherein at least a portion of an external surface of a covering of the container is transparent to permit inspection of the stored airway device.

The invention further includes the embodiments of such airway device kits wherein a portion of an external surface of a covering of the container comprises:

(A) an Information Panel that provides a user with information regarding the stored airway device;

(B) a Sensor Panel that provides a user with information regarding a functionality of the stored airway device; or (C) an Auxiliary Panel that provides a user with means to heat or to illuminate the stored airway device.

The invention further includes the embodiments of such airway device kits wherein a covering of the container contains an embedded material, which, when pulled, causes the external surface to tear, and thereby permits retrieval of the stored airway device and/or wherein a covering of the container is pseudo-perforated such that when the pseudo-perforations are stressed, the external surface tears, and thereby permits retrieval of the stored airway device.

The invention further includes the embodiments of such airway device kits wherein the kit additionally comprises a hypoallergenic strap, tape, sterile non-allergenic gloves or an LED flashlight.

The invention further includes the embodiments of such airway device kits wherein the kit additionally comprises an oxygen source.

The invention further includes the embodiments of such airway device kits wherein the airway device comprises a cuff capable of self-inflation or a cuff connected to an air-filled, manual or self-actuating syringe.

DETAILED DESCRIPTION OF THE INVENTION

The present invention relates to a packaging system for airway devices that permits their rapid access. In particular, the packaging system is capable of maintaining the device in storage under sterile conditions, yet be capable of facilitating rapid unpackaging and use.

In a preferred embodiment, the packaging system would be formed of paper or plastic, and comprise a container (as used herein, the term container is intended to denote any closed container, such as a pouch, tube, envelope, etc.) suitable for receiving the airway device. Preferably, the material would be biodegradable and obtained from a renewable resource. Additionally, the material packaging preferably will be hypoallergenic, non-traumatic, treated to be fire-retardant (or more preferably, fireproof), waterproof and pliable (so as to provide ease of use even under conditions of low or extreme temperature, etc.). In preferred embodiments, the packaging system would be formed of a material treated to be bacteriostatic, bacteriocidal, fungistatic and/or fungicidal.

Such packaging may, for example, be formed from a paper construction in which the paper is grid-lacquered with polyethylene and welded around its edge to a laminate of, for example, polyethylene-polypropylene, polyethylene-polyetheylene terephthalate of possibly polyetheylene-nylon (see, e.g., U.S. Pat. Nos. 4,941,308; 4,863,016). The dimensions of the system will vary so as to provide dimensions suitable for the device to be enclosed therein.

Typically, the system will be fabricated to be capable of withstanding sterilization procedures, and of thereafter maintaining the enclosed medical device in a sterile condition. Although procedures such as autoclaving may be employed (depending upon the capability of the enclosed device to withstand such treatment), it is preferred to employ radiative sterilization means (e.g., ion bombardment, ionizing light, etc.) or gaseous sterilization means (e.g., ethylene oxide exposure) to sterilize the internal cavities and surfaces of the system and its enclosed device.

Besides maintaining a medical device's sterility, the packaging system will preferably possess the ability to reveal by inspection whether the package has been tampered with. Thus, for example, the packaging system will typically be designed such that upon receipt of the desired medical device, it can be permanently closed via application of heat, pressure, etc. to thereafter preclude access to the device until needed.

Figure 1:
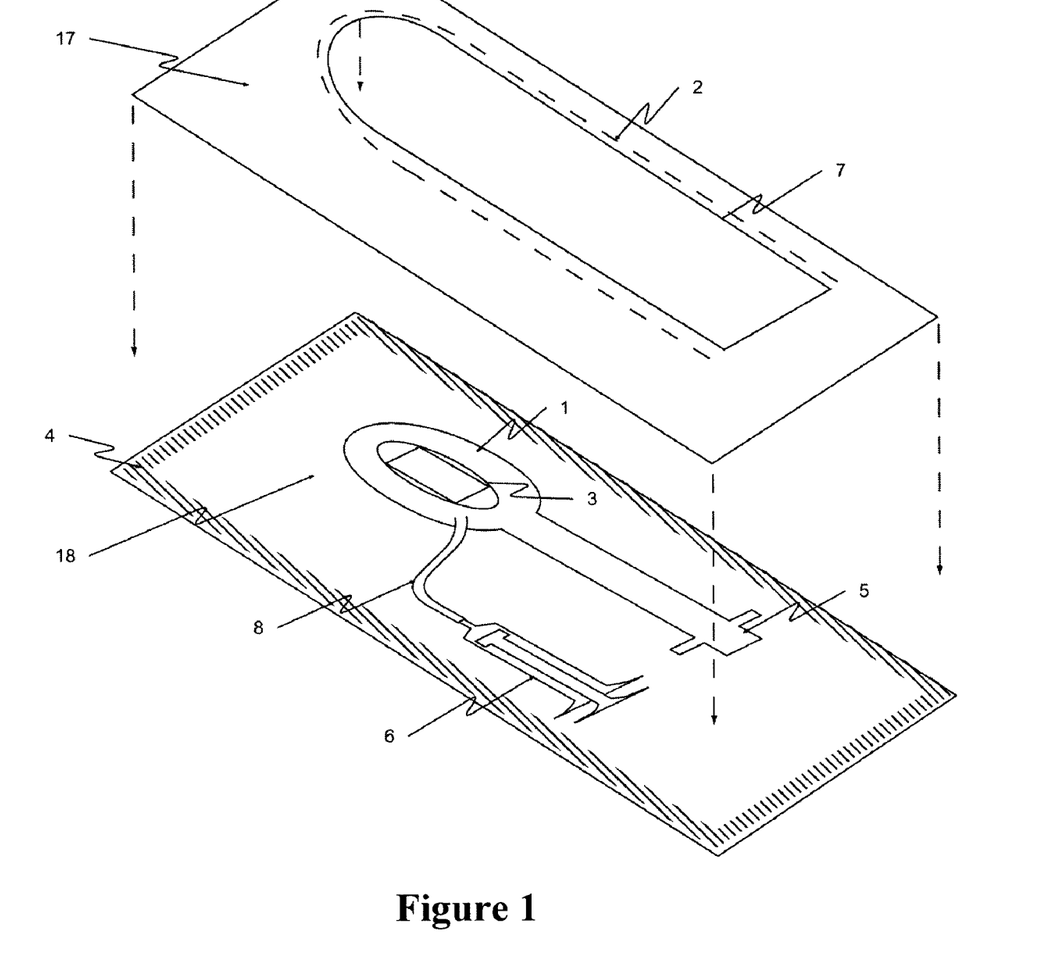
FIG. 1 illustrates a first preferred embodiment of the packaging system of the present invention. The illustrated packaging system comprises an upper covering 17 and a lower covering 18. The airway device to be enclosed in the packaging system is disposed between these coverings, which are then sealed to one another via contact at region 4.

Preferred embodiments of the invention are illustrated herein by reference to the Figures. FIG. 1 shows an illustrative airway device and packaging system of the present invention. Although the packaging system of the present invention does not require or employ any particular design of airway device, for purposes of illustration, the packaging system is shown as containing an airway device having an inflatable cuff 1 connected to a tube 5, and a syringe 6 for inflating the cuff 1 through interconnecting tube 8.

As shown in FIG. 1, an exemplary packaging system of the present invention can be formed by contacting internal surfaces of an upper covering 17 and a lower covering 18 at region 4, so as to create a container which sandwiches the airway device between the internal surfaces of such upper and lower coverings. The external surfaces of such coverings are exposed to the environment and are viewable by a user without opening the packaging system.

Although, for ease of description, the packaging system of the present invention is thus described as being formed from the contacting of two coverings, it will be understood that other means for creating a suitable container may be employed. For example, a suitable container can be formed by folding a single covering upon itself and sealing the three (or all) contacting sides. Alternatively, a suitable container can be formed by fashioning (e.g., rolling) a single sheet to form a tube and then sealing the tube along its length and at its ends. Multiple equivalent approaches can be used to produce the container of the packaging system of the present invention. In one embodiment, the packaging system may itself be packaged in a further container.

Figure 2:
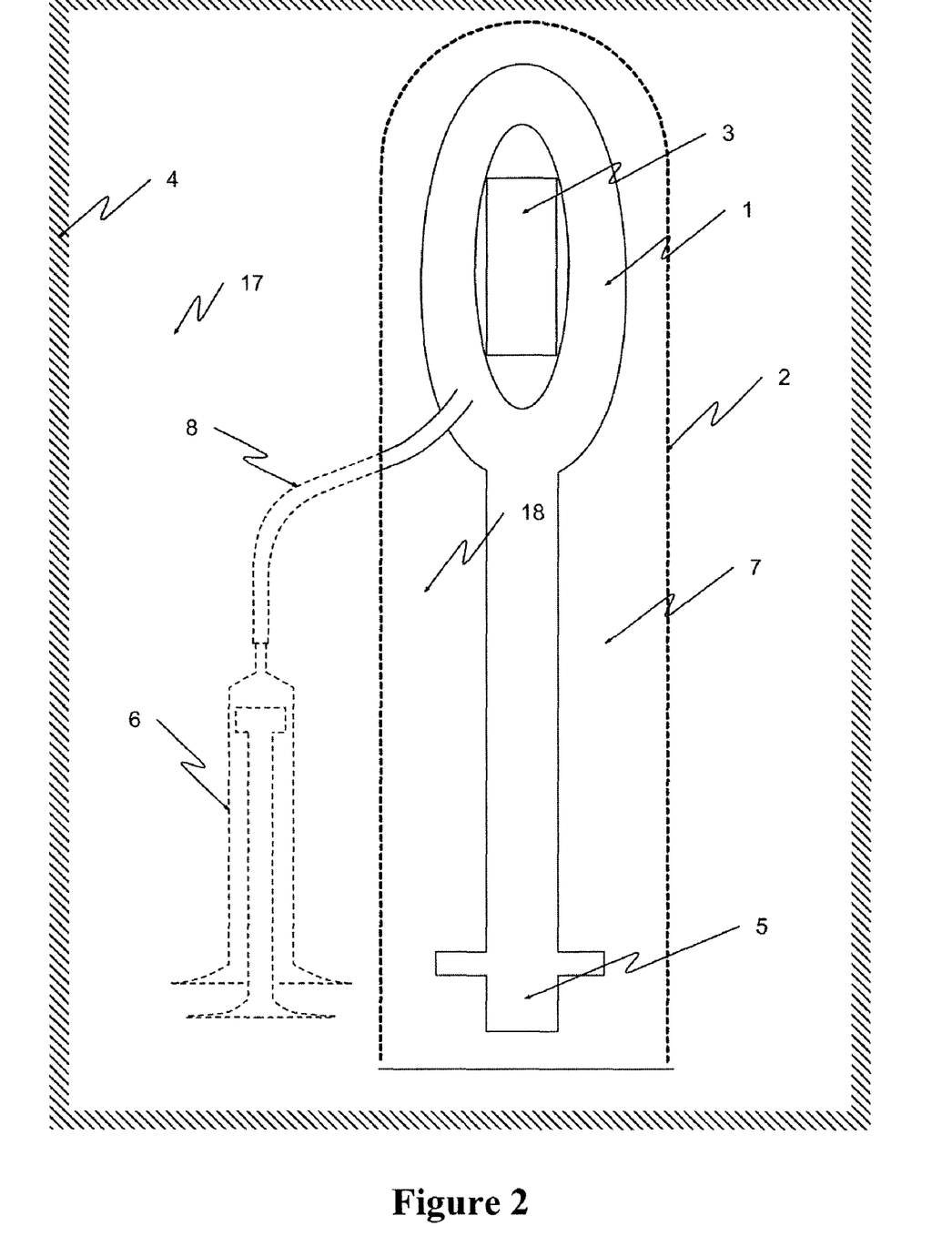
FIG. 2 illustrates a first preferred embodiment of the packaging system of the present invention. The Figure illustrates a top-down view of the internal surface of the lower covering 18 of the packaging system of the present invention, shown containing an exemplary airway device.

FIG. 2 illustrates an embodiment of such a sealed packaging system, looking top down through the upper covering 17 to the internal surface of lower covering 18. The lower covering 18 and the upper covering 17 of the illustrative container contact each other at region 4 to form a sterilizable seal. A transparent region 7 of upper covering 17 permits one to view the enclosed airway device. The dimensions and location of transparent region 7 are not critical, but are preferably designed to permit the user to readily identify and confirm that the package contains the desired airway device and, in more preferred embodiments, to determine significant attributes of the enclosed device (e.g., size of cuff, maintenance of sterile environment, etc.). If desired the coverings of the container may be completely transparent or transparent region 7 of upper covering 17 may be so large in dimension as to render the substantially the entire covering transparent.

Syringe 6 and interconnecting tube 8, which are used in certain embodiments to inflate cuff 1 are shown using dotted lines because they are covered by a non-transparent region of upper covering 18 of the packaging system. Syringe 6 is preferably stored inside of the packaging system (as shown) however, it may alternatively be outside of packaging system 4 or may be deleted from the packaging system altogether.

The cuff 1 of the enclosed device may be self-inflating, such as, for example, capable of self-inflation when warmed (e.g., after insertion into the patient), or may be connected to a syringe capable of self-activating to inflate the cuff. This could be accomplished by a drive gas contained in the cuff, which would fill the cuff when activated.

Figure 3:
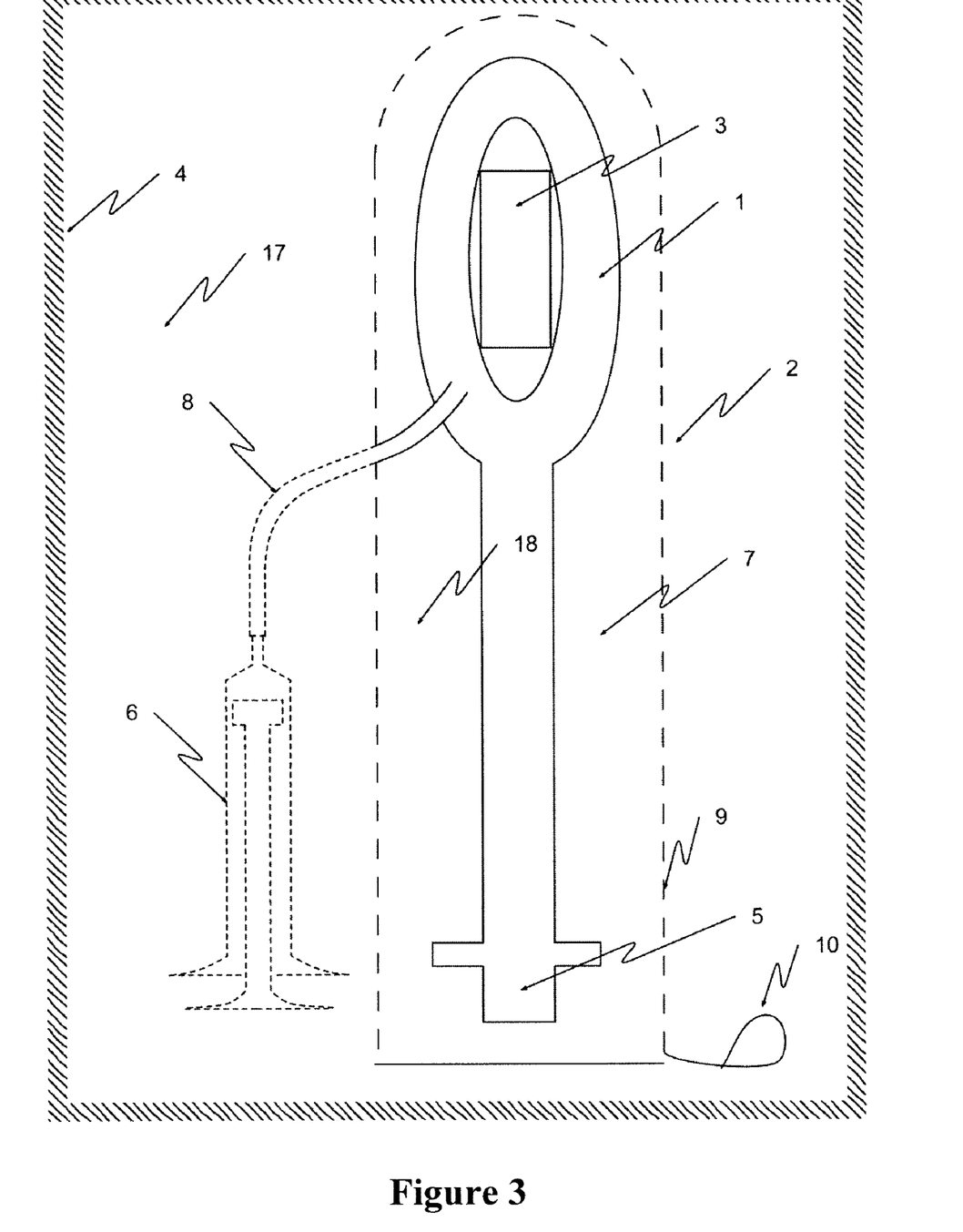
FIG. 3 illustrates a second preferred embodiment of the packaging system of the present invention. The Figure illustrates a top-down view of the internal surface of the lower covering 18 of the packaging system, shown containing an exemplary airway device.
Figure 4:
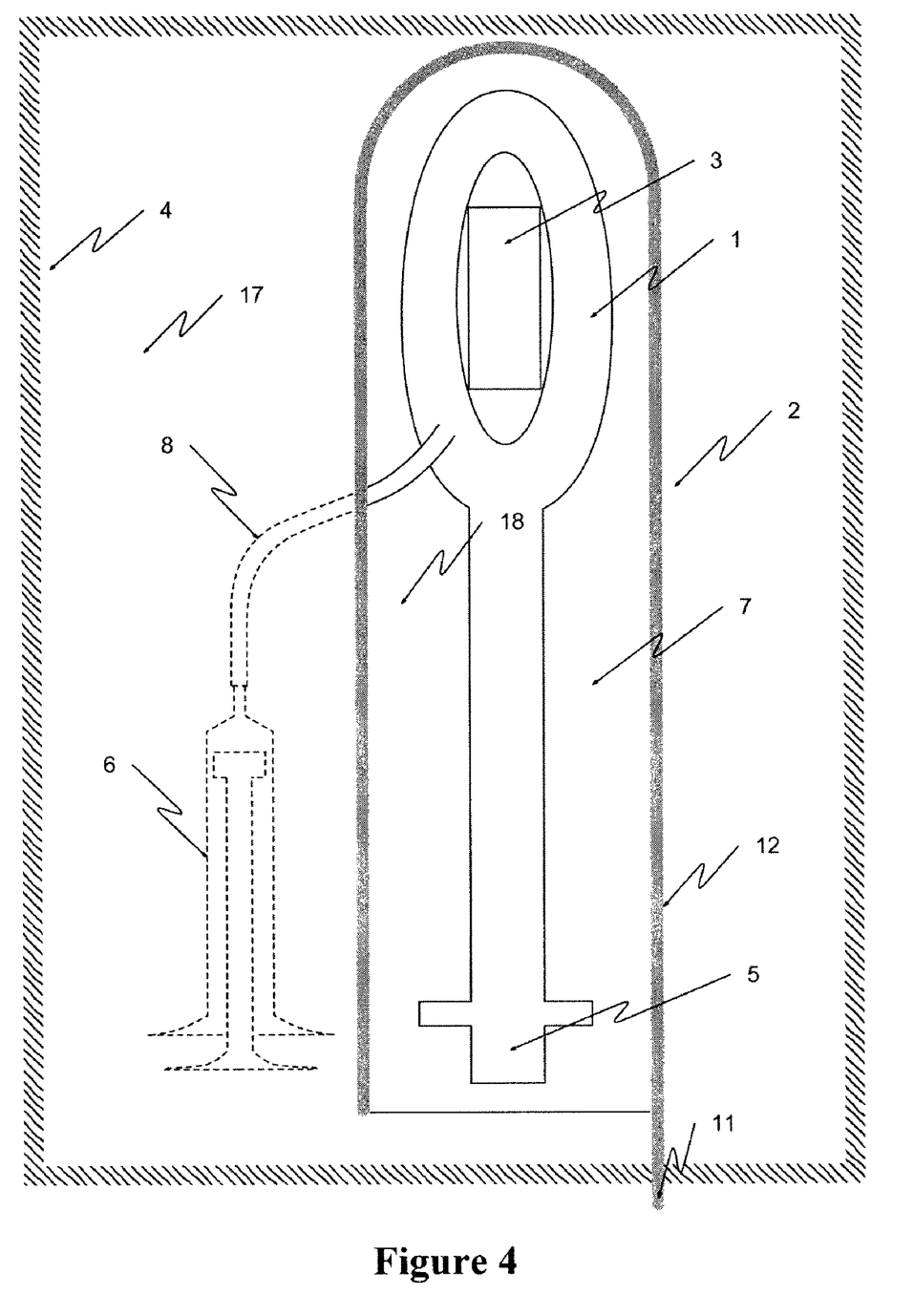
FIG. 4 illustrates a third preferred embodiment of the packaging system of the present invention. The Figure illustrates a top-down view of the internal surface of the lower covering 18 of the packaging system, shown containing an exemplary airway device.

Regardless of its shape, the packaging system will comprise a means for rapidly opening the package to permit removal of the airway device. Any of a variety of means may be employed to permit such rapid opening. For example, as shown in FIG. 2, the packaging may be prestressed, embossed, etc. so as to be pseudo-perforated 2 (i.e., maintaining sterility, but capable of being torn as though perforated). Alternatively, as shown in FIG. 3, a thread or cord 9 (e.g., of unbreakable nylon) may be incorporated into upper covering 17 of the packaging system in a desired design or configuration 2, such that the upper covering 17 will tear in a pattern consistent with such design or configuration when end 10 of the cord is pulled. Alternatively, as shown in FIG. 4, the packaging may possess a protruding tab 11, which when pulled, would cause the packaging system to tear open in a predetermined manner along a region of reinforced material 12 having a desired design or configuration 2. For example, the tab could comprise a part of a region of the packaging system (reinforced as with nylon, plastic, paper, cardboard, etc.) whose boundaries were composed of, or separated by, an intervening non-reinforced material.

In an embodiment preferred in packaging systems that comprise an airway device, the packaging system will additionally include a lubricant 3 (preferably non-allergenic) stored, for example, in a pressure-repturable container. Application of pressure to the container causes the container to rupture and thereby provide itself as a layer of lubrication on the cuff 1, facilitating its insertion into the patient. Most preferably, such rupturing and auto-lubrication of the cuff 1 can be accomplished once the packaging device has been opened.

Figure 5:
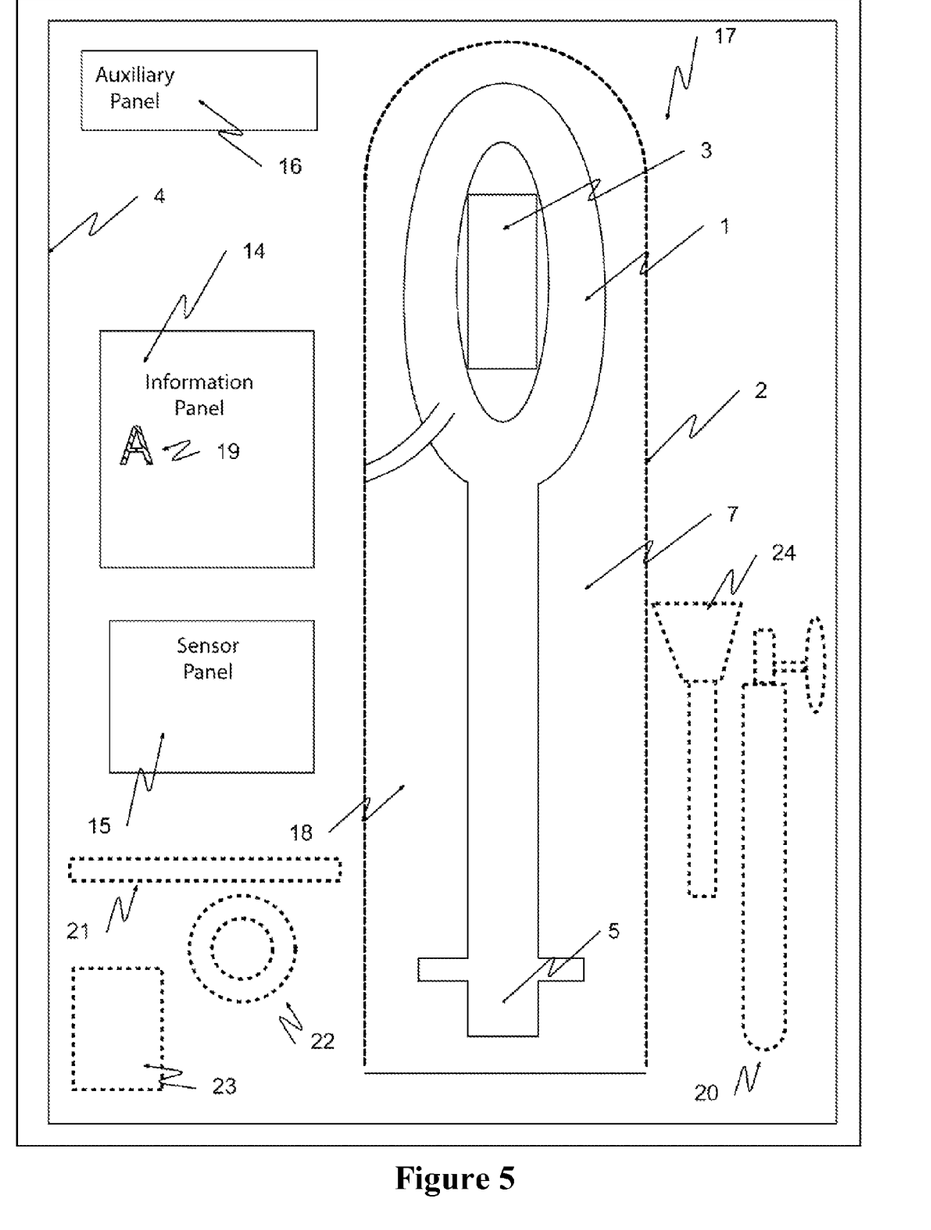
FIG. 5 illustrates a top-down view of the external surface of the upper covering 17 of the first preferred embodiment of the packaging system of the present invention, shown containing an exemplary airway device. The Figure illustrates the placement of the transparent region, and the presence of an Information Panel, an Auxiliary Panel and a Sensor Panel.

FIG. 5 illustrates the packaging system of FIG. 2 in which the view of the enclosed airway device is covered (except for transparent region 7) by the upper covering 17 of the system. FIG. 4 illustrates several additional optional embodiments of the packaging system of the present invention. In preferred embodiments, the packaging system will contain an Informational Panel 14, which displays information relating to the nature, size (e.g., child or adult, or height or weight ranges of the intended recipient patient, or of support or contact information), expiration date, lot number, etc. of the enclosed device. In preferred embodiments, the packaging system (and particularly the Information Panel 14 thereof) will be coded (as by possessing a pre-determined panel color, panel shape, panel texture, etc.) so as to permit the user to more rapidly ascertain important information regarding the enclosed device. For example, a packaging system containing a device sized for a child might have an Informational Panel 14 that would be colored green, be hexagonal in shape, or be ribbed or rough textured.

Particularly for devices (such as the exemplary airway devices depicted in the Figures) that may need to be deployed under emergency settings of low light, the packaging system of the present invention may be adapted to include attributes for facilitating proper selection under such conditions. Thus, as discussed above, the Information Panel 14, or a portion 19 thereof, may be textured (e.g., ribbed, tabbed, embossed, smooth, rough, etc.). Optionally, such texturizing may be shaped into letters, numbers, patterns, etc.

In one embodiment, the packaging will have one or more Sensor Panel(s) 15, whose placement(s) and dimensions may vary depending upon the number of such panels present, upon the nature of individual panels and upon their function(s), but which will preferably be located on the upper covering 17 of the packaging device. Although such Sensor Panel(s) 16 are described below with respect to only a single function, such is for ease of depiction alone. Thus, a Sensor Panel 15 may provide a single functionality, or may provide multiple functionalities.

In one embodiment, a Sensor Panel 15 may be provided that will contain a temperature sensor (e.g., a liquid crystal thermometer (see, e.g., U.S. Pat. No. 6,257,759), or a battery-powered thermometer having an LED display (see. e.g., U.S.

Pat. Nos. 5,165,798; 5,829,878; 5,923,258; 6,441,726; 6,778,095 or 7,350,973), etc.) suitable for measuring the ambient temperature or the temperature of the packaged airway device.

In a further embodiment, a Sensor Panel 15 may be provided that will contain a carbon dioxide detection sensor (see, e.g., U.S. Pat. No. 6,365,022 or 5,194,134) suitable for determining the partial pressure of carbon dioxide being exhaled by the recipient patient.

In one embodiment, the packaging will have one or more Auxiliary Panels 16, whose placement(s) and dimensions may vary depending upon the number of such panels present, upon the nature of individual panels and upon their function (s), but which will preferably be located on the upper covering 17 of the packaging device. Although such Auxiliary Panels 16 are described below with respect to only a single function, such is for ease of depiction alone. Thus, an Auxiliary Panel 16 may provide a single functionality, or may provide multiple functionalities.

In one embodiment, an Auxiliary Panel 16 may be provided that will contain an embedded illumination means to facilitate low light viewing of the package. Such means may include electrically powered lights (for example a flashlight powered by a battery integrated, for example, into the upper covering 17 of the packaging system along with a pressure activated switch). Flashlights having LED bulbs are preferred due to their durability and longevity. Alternatively, illumination may be provided by embedded pressure rupturable containers (e.g., bags, tubes, etc.) having contents that, upon rupture of the containers, mix to produce chemoluminescent or bioluminescent light (see, e.g., U.S. Pat. Nos. 6,914,250; 6,690,619; 6,637,924; 6,247,995; 6,152,358; 6,113,886; 5,876,995; 5,083,242; 4,717,511; 4,678,608; 4,379,320; 3,539,794; 3,591,362).

In a further embodiment, an Auxiliary Panel 16 may be provided that will contain an embedded heating means to facilitate warming the enclosed device to physiological temperature (e.g., 37° C.). Such means may include embedded pressure rupturable containers (e.g., bags, tubes, etc.) having contents that, upon rupture of the containers, mix to produce an exothermal reaction (e.g., sodium acetate and water; calcium chloride and water; magnesium sulfate and water; glycerin and water; cellulose, iron, water, activated carbon, vermiculite and salt that produce heat from the exothermic oxidation of iron when the container is ruptured and thus exposed to air; etc.).

In a further embodiment, the packaging system of the present invention may comprise an oxygen source 20 (e.g., an oxygen tank, oxygen generator, oxygen concentrator, etc.) suitable for providing oxygen to the recipient patient.

In a further embodiment, the packaging system of the present invention may comprise one or more articles (e.g., hypoallergenic straps 21 or tape 22 suitable for securing the airway device upon its installation to the recipient patient; sterile non-allergenic gloves 23, an LED flashlight 24 capable of separation from the packaging and sufficient to permit the user installing the device to more easily observe the airway of the recipient patient.

In a further embodiment, the packaging system of the present invention may comprise instructions for opening the packaging system or instructions for application and use of the device enclosed therein. Preferably, such instructional information will be pictorial so as to be readily comprehended regardless of the language(s) understood by users.

The present invention is additionally directed to airway device kits, which comprise an airway device disposed within the above-described containers of the packaging system of the present invention.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A packaging system for sterilely storing an airway device, wherein said system comprises a covering capable of being sealed to itself, or to a second covering, to thereby form a closed container for sterilely storing said airway device; wherein said container possesses an external surface that has been specially adapted to permit a user to tear open the container and retrieve the stored airway device and wherein a portion of an external surface of a covering of said container comprises an Auxiliary Panel that provides a user with means to heat or to illuminate a stored airway device.

2. The packaging system of claim 1, wherein said closed container is formed from a single covering sealed upon itself.

3. The packaging system of claim 1, wherein said closed container is formed from sealing a first covering to a second covering.

4. The packaging system of claim 1, wherein a portion of an external surface of a covering of said container is transparent to permit inspection of a stored airway device.

5. The packaging system of claim 1, wherein a portion of an external surface of a covering of said container comprises an Information Panel that provides a user with information regarding an airway device to be stored in said container.

6. The packaging system of claim 5, wherein said information is partially provided as a color, a shape, or a texture.

7. The packaging system of claim 1, wherein a covering of said container contains an embedded material, which, when pulled, causes said external surface to tear, and thereby permit retrieval of a stored airway device.

8. The packaging system of claim 1, wherein a covering of said container is pseudo-perforated such that when said pseudo-perforations are stressed, said external surface tears, and thereby permit retrieval of a stored airway device.

9. The packaging system of claim 1, wherein a portion of an external surface of a covering of said container comprises a Sensor Panel that provides a user with information regarding a functionality of an airway device to be stored in said container.

10. The packaging system of claim 9, wherein said Sensor Panel displays:
    (A) the partial pressure of carbon dioxide being exhaled by the recipient patient; or
    (B) the temperature of the airway device.

11. The packaging system of claim 1, wherein said system additionally comprises a hypoallergenic strap, tape, sterile non-allergenic gloves, or an LED flashlight.

12. An airway device kit, comprising an airway device sterilely enclosed in a closed container, wherein said container is formed from a covering sealed to itself or to a second covering, wherein a covering of said container possesses an external surface that has been specially adapted to permit a user to tear open the container and retrieve the stored airway device and wherein a portion of an external surface of a covering of said container comprises an Auxiliary Panel that provides a user with means to heat or to illuminate a stored airway device.

13. The airway device kit of claim 12, wherein a portion of an external surface of a covering of said container is transparent to permit inspection of the stored airway device.

14. The airway device kit of claim 12, wherein a portion of an external surface of a covering of said container comprises:
   (A) an Information Panel that provides a user with information regarding the stored airway device;
   (B) a Sensor Panel that provides a user with information regarding a functionality of said airway device; or
   (C) an Auxiliary Panel that provides a user with means to heat or to illuminate said airway device.

15. The airway device kit of claim 12, wherein a covering of said container contains an embedded material, which, when pulled, causes said external surface to tear, and thereby permits retrieval of the stored airway device.

16. The airway device kit of claim 12, wherein a covering of said container is pseudo-perforated such that when said pseudo-perforations are stressed, said external surface tears, and thereby permits retrieval of the stored airway device.

17. The airway device kit of claim 12, wherein said kit additionally comprises a hypoallergenic strap, tape, sterile non-allergenic gloves or an LED flashlight.

18. The airway device kit of claim 12, wherein said kit additionally comprises an oxygen source.

19. The airway device kit of claim 12, wherein said airway device comprises a cuff capable of self-inflation or a cuff connected to an air-filled, manual or self-actuating syringe.

20. The airway device kit of claim 12, wherein said kit additionally comprises a lubricant.

* * * * *